(12) United States Patent
Traynor et al.

(10) Patent No.: US 9,192,548 B2
(45) Date of Patent: *Nov. 24, 2015

(54) CERAMIC ENCAPSULATION WITH CONTROLLED LAYERING BY USE OF FUNCTIONALIZED SILANES

(75) Inventors: Daniel H. Traynor, Sarasota, FL (US); Hao Xu, Canton, MI (US); Henry G. Traynor, Sarasota, FL (US); Daniel H. Traynor, legal representative, Sarasota, FL (US); John Carson, Union City, NJ (US); Martin S. Flacks, Danville, CA (US); Rachel Sullivan, Addison, TX (US)

(73) Assignee: CoLabs International Corporation, Las Vegas, NV (US)

( * ) Notice: Subject to any disclaimer, the term of this patent is extended or adjusted under 35 U.S.C. 154(b) by 282 days.

This patent is subject to a terminal disclaimer.

(21) Appl. No.: 13/168,715

(22) Filed: Jun. 24, 2011

(65) Prior Publication Data

US 2012/0107499 A1    May 3, 2012

Related U.S. Application Data

(60) Provisional application No. 61/358,733, filed on Jun. 25, 2010.

(51) Int. Cl.
*B01J 13/22*    (2006.01)
*A61K 8/11*    (2006.01)
(Continued)

(52) U.S. Cl.
CPC ................ *A61K 8/11* (2013.01); *A61K 8/0279* (2013.01); *A61K 8/585* (2013.01); *A61Q 19/00* (2013.01)

(58) Field of Classification Search
CPC .... B22F 2999/00; B22F 1/0018; B22F 1/025; B22F 1/0051; B22F 1/0062; B22F 2001/0029; B82Y 30/00; B82Y 5/00; B82Y 20/00; B82Y 25/00; C08L 83/04; A61K 9/5115; A61K 2800/623; A61K 47/02
USPC .............. 427/331, 389.9, 212, 213.3–213.36, 427/483, 256, 2.14, 2.31, 8, 385.5; 264/534, 41, 4–4.7, 4.32, 4.1, 4.2, 264/4.33, 4.4; 424/59, 60, 63, 400, 408, 424/450, 451, 455, 93.7, 184.1, 497, 489, 424/501, 490, 491, 492, 493, 494, 495; 501/158, 106; 428/321.5, 402–402.24, 428/403, 404, 407
See application file for complete search history.

(56) References Cited

U.S. PATENT DOCUMENTS 5,126,061 A    6/1992  Michael
5,387,622 A    2/1995  Yamamoto (Continued)

*Primary Examiner* — James J Seidleck
*Assistant Examiner* — S. Camilla Pourbohloul
(74) *Attorney, Agent, or Firm* — One3 IP Management, P.C.; Dean G. Stathakis; Peter D. Weinstein

(57) ABSTRACT

This invention relates to a method for forming hollow silica-based particles suitable for containing one or more active ingredients or for containing other smaller particles which may include one or more active ingredients. The method comprises preparing an emulsion including a continuous phase that is polar or non-polar and a dispersed phase comprising droplets including (i) a polar active ingredient when the continuous phase is non-polar or (ii) a non-polar active ingredient when the continuous phase is polar; and adding a silica precursor to the emulsion such that the silica precursor can be emulsion templated on the droplets to form hollow silica-based particles. The silica precursor has the general formula (I): $R^1_x$—Si—$(OR^2)_y$, wherein $R^1$ is selected from substituted and unsubstituted alkyl, substituted and unsubstituted aryl, alcohols, amines, amides, aldehydes, acids, esters, and functional groups having an unsaturated carbon-carbon bond, $R^2$ is an alkyl group, $x+y=4$, and $y=1$, 2 or 3. The —$OR^2$ group is a hydrolyzable organic group that exhibits an ability to form a silicon-oxygen bond chain as a result of hydrolysis and condensation.

25 Claims, 3 Drawing Sheets

(51) Int. Cl.
  *A61K 8/58*   (2006.01)
  *A61Q 19/00*  (2006.01)
  *A61K 8/02*   (2006.01)

(56) References Cited

U.S. PATENT DOCUMENTS

| | | | |
|---|---|---|---|
| 6,251,313 B1 | 6/2001 | Deubzer et al. | |
| 6,468,509 B2 | 10/2002 | Lapidot et al. | |
| 6,855,335 B2 * | 2/2005 | Seok et al. | 424/489 |
| 6,998,113 B1 | 2/2006 | Traynor et al. | |
| 7,001,592 B1 | 2/2006 | Traynor et al. | |
| 7,025,952 B1 | 4/2006 | Traynor et al. | |
| 7,037,513 B1 | 5/2006 | Traynor et al. | |
| 7,153,525 B1 | 12/2006 | Mumper et al. | |
| 7,226,581 B2 | 6/2007 | Traynor et al. | |
| 7,226,582 B2 | 6/2007 | Traynor et al. | |
| 7,563,451 B2 | 7/2009 | Lin et al. | |
| 2003/0157330 A1 | 8/2003 | Ostafin et al. | |
| 2004/0091411 A1 | 5/2004 | Modrek-Najafabadi | |
| 2006/0018966 A1 | 1/2006 | Lin et al. | |
| 2006/0167147 A1 | 7/2006 | Asgari | |
| 2006/0173709 A1 | 8/2006 | Traynor et al. | |
| 2006/0292345 A1 | 12/2006 | Dave et al. | |
| 2007/0036736 A1 * | 2/2007 | Kalla et al. | 424/63 |
| 2007/0292676 A1 | 12/2007 | Naigertsik et al. | |
| 2008/0112904 A1 | 5/2008 | Traynor et al. | |
| 2008/0199523 A1 * | 8/2008 | Finnie et al. | 424/484 |
| 2008/0233509 A1 | 9/2008 | Keoshkerian et al. | |
| 2008/0317795 A1 * | 12/2008 | Traynor et al. | 424/401 |
| 2010/0016200 A1 | 1/2010 | Nagare et al. | |
| 2010/0143422 A1 | 6/2010 | Popplewell et al. | |
| 2010/0247660 A1 | 9/2010 | Lei et al. | |

* cited by examiner

CERAMIC ENCAPSULATION WITH CONTROLLED LAYERING BY USE OF FUNCTIONALIZED SILANES

CROSS-REFERENCES TO RELATED APPLICATIONS

This application claims priority from U.S. Patent Application No. 61/358,733 filed Jun. 25, 2010.

STATEMENT REGARDING FEDERALLY SPONSORED RESEARCH

Not Applicable.

BACKGROUND OF THE INVENTION

1. Field of the Invention

This invention relates to a method for forming hollow silica-based particles suitable for containing one or more active ingredients or for containing other smaller particles which can include one or more active ingredients.

2. Description of the Related Art

One approach to providing an active ingredient to a surface, such as the skin, is to encapsulate the active ingredient in order to protect the active ingredient, control the release of the active ingredient, and/or modify the function of the active ingredient. Methods for encapsulation of an active ingredient, such as sol-gel encapsulation, are known in the art. See, for example U.S. Patent Application Publication No. 2008/0317795 to Traynor et al.

Even with the advances in the art described in U.S. 2008/0317795, there is still a need for further improved encapsulation techniques.

SUMMARY OF THE INVENTION

The present invention provides a method for forming silica-based particles that encapsulate one or more active ingredients or encapsulate other smaller particles which can include one or more active ingredients. The method uses multifunctional silanes for particle encapsulation. The silanes include functional groups such as: (1) lipophilic: aryls (e.g., phenyl); alkyls (e.g., behenyl, octyl, dodecyl, cetyl, stearyl, $C_{12}$-$C_{24}$ alkyl); (2) vinyl (e.g., acrylic acid); and (3) hydrophilic (e.g., polyethylene glycol, long chain alkylamine, carboxylates). The hollow shell layering can be controlled by the functional groups (such as phenyl and amine) that can block the encapsulation reaction, i.e., the thickness is varied by blocking groups that stop the reaction. Also, functional groups (such as phenyl) can align at the continuous phase/dispersed phase interface and form pores, i.e., the porosity is controlled by the functionalized silanes. In addition, varying ratios of secondary silanes can stop the encapsulation reaction (to form thinner walls), or make the particles cationic, or make the particles hydrophobic, and can control thicknesses of the walls of the particles (e.g., 2-60 nm). Three secondary silanes can also be beneficial (e.g., two cationics for net charge—0-80 mV zeta) for controlling reaction, or making cationic, or making hydrophobic.

In one aspect, the invention provides method for forming hollow silica-based particles. The method comprises preparing an emulsion including a continuous phase that is polar or non-polar and a dispersed phase comprising droplets including (i) a polar active ingredient when the continuous phase is non-polar or (ii) a non-polar active ingredient when the continuous phase is polar; and adding a silica precursor to the emulsion such that the silica precursor can be emulsion templated on the droplets to form hollow silica-based particles. The silica precursor has the general formula (I):

$$R^1_x\text{—Si—}(OR^2)_y \qquad (I)$$

wherein $R^1$ is selected from substituted and unsubstituted alkyl, substituted and unsubstituted aryl, alcohols, amines, amides, aldehydes, acids, esters, and functional groups having an unsaturated carbon-carbon bond, wherein $R^2$ is an alkyl group, wherein x+y=4, and wherein y=1, 2 or 3. In general, the —$OR^2$ group is a hydrolyzable organic group that exhibits an ability to form a silicon-oxygen bond chain as a result of hydrolysis and condensation. Preferably, y=3, $R^1$ is selected from substituted and unsubstituted alkyl, substituted and unsubstituted aryl, functional groups having an unsaturated carbon-carbon bond, functional groups having a carboxylic acid group, and aminofunctional groups, and $R^2$ is $C_1$ to $C_5$ alkyl.

Optionally, the method further includes the step of adding a second silica precursor to the emulsion such that the second silica precursor can be emulsion templated on the droplets or deposited on the hollow silica-based particles to form hollow silica-based particles, wherein the second silica precursor has the general formula (II):

$$R^3_m\text{—Si—}(OR^4)_n \qquad (II)$$

wherein $R^3$ is selected from substituted and unsubstituted alkyl, substituted and unsubstituted aryl, alcohols, amines, amides, aldehydes, acids, esters, and functional groups having an unsaturated carbon-carbon bond, wherein $R^4$ is an alkyl group, wherein m+n=4, and wherein m=0, 1, 2 or 3. In general, the —$OR^4$ group is a hydrolyzable organic group that exhibits an ability to form a silicon-oxygen bond chain as a result of hydrolysis and condensation. Preferably, m=0, $R^3$ is selected from substituted and unsubstituted alkyl, substituted and unsubstituted aryl, functional groups having an unsaturated carbon-carbon bond, functional groups having a carboxylic acid group, and aminofunctional groups, and $R^4$ is $C_1$ to $C_5$ alkyl.

Optionally, the method further includes the step of adding a third silica precursor to the emulsion such that the third silica precursor can be emulsion templated on the droplets or deposited on the hollow silica-based particles to form hollow silica-based particles, wherein the third silica precursor has the general formula (III):

$$R^5_a\text{—Si—}(OR^6)_b \qquad (III)$$

wherein $R^5$ is selected from substituted and unsubstituted alkyl, substituted and unsubstituted aryl, alcohols, amines, amides, aldehydes, acids, esters, and functional groups having an unsaturated carbon-carbon bond, wherein $R^6$ is an alkyl group, wherein a+b=4, and wherein a=0, 1, 2 or 3. In general, the —$OR^6$ group is a hydrolyzable organic group that exhibits an ability to form a (silicon-oxygen) bound chain as a result of hydrolysis and condensation. Preferably, a=0, $R^5$ is selected from substituted and unsubstituted alkyl, substituted and unsubstituted aryl, functional groups having an unsaturated carbon-carbon bond, functional groups having a carboxylic acid group, polymers of alkylene oxide, and aminofunctional groups, and $R^6$ is $C_1$ to $C_5$ alkyl.

In certain versions of the above methods of the invention, $R^1$ and/or $R^3$ and/or $R^5$ can be phenyl; $R^1$ and/or $R^3$ and/or $R^5$ and/or be $C_{12}$-$C_{24}$ alkyl; $R^1$ and/or $R^3$ and/or $R^5$ can be substituted or unsubstituted acrylic acid; $R^1$ and/or $R^3$ and/or $R^5$ can be polyethylene glycol; $R^1$ and/or $R^3$ and/or $R^5$ can be alkylamine; $R^1$ and/or $R^3$ and/or $R^5$ can be alkyl carboxylate; or $R^1$ and/or $R^3$ and/or $R^5$ can be alkyl quaternary amine.

The method of the invention can use an oil in water emulsion that includes an aqueous continuous phase; a dispersed phase comprising droplets including a non-polar material and/or one or more oils; and the silica precursor and/or the second silica precursor and/or the third silica precursor defined above. The present invention also provides an emulsion templated silica particle formed from the oil in water emulsion of the invention wherein the silica particle can be modified from a continuously formed shell to a partially formed hollow shell by adjusting a ratio of the silica precursors in the emulsion.

Alternatively, the method of the invention can use a water-in-oil emulsion that includes a non-polar, aqueous immiscible, "oil" continuous external phase; a dispersed internal phase comprising droplets including a polar active ingredient and optionally one or more other polar materials such as water; and the silica precursor and/or the second silica precursor and/or the third silica precursor defined above. The present invention also provides an emulsion templated silica particle formed from the water-in-oil emulsion of the invention wherein the silica particle can be modified from a continuously formed shell to a partially formed hollow shell by adjusting a ratio of the silica precursors in the emulsion.

The present invention also provides an oil-in-water emulsion or water-in-oil emulsion for making silica coated particles. The oil-in-water emulsion or water-in-oil emulsion can include a surfactant component comprising a surfactant selected from anionic surfactants, nonionic surfactants, cationic surfactants, nonionic surfactants, and mixtures thereof, each surfactant in the surfactant component being above or below a critical micelle concentration of each surfactant; a continuous phase (i.e., water in the oil-in-water emulsion, or oil in the water-in-oil emulsion) that forms droplets of a dispersed phase (i.e., oil in the oil-in-water emulsion, or water in the water-in-oil emulsion); and the silica precursor and/or the second silica precursor and/or the third silica precursor defined above.

The hollow silica-based particles of the invention are suitable for encapsulating one or more active ingredients. Non-limiting example products in which the particles including an active ingredient can be used include: cosmetic products, such as skin cream and sunscreen formulations; detergent products such as laundry wash products, household cleaners, shampoos, hair conditioners and bleaches; and oral hygiene products such as toothpastes. Depending upon the product and its use, the particles may be employed to protect the active ingredient against loss by evaporation during storage or against chemical degradation by other ingredients in the formulation, to improve the targeting of materials in use (e.g., perfume deposition onto fabrics during washing), to assist controlled delivery through heat or dissolution, or to extend activity (e.g. of a fragrance or flavoring) through controlled delivery and evaporation.

It is an advantage of the invention to provide a method for encapsulation of an active ingredient in hollow silica-based particles in which unencapsulated particles formed in the method are minimized.

It is another advantage of the invention to provide a method for encapsulation of an active ingredient in hollow silica-based particles in which the particles do not need to be post-loaded with the active ingredient.

It is another advantage of the invention to provide a method for encapsulation of an active ingredient in hollow silica-based particles in which the reaction time is minimized in relation to other encapsulation methods.

It is another advantage of the invention to provide a method for encapsulation of an active ingredient in hollow silica-based particles in which Stoeber particles are minimized.

It is another advantage of the invention to provide a method for encapsulation of an active ingredient in hollow silica-based particles in which the resulting particles do not become brittle when dried.

It is another advantage of the invention to provide a method for encapsulation of an active ingredient in hollow silica-based particles in which the particles have a surface functionality or a chargeable surface for attachment of additional molecules.

These and other features, aspects, and advantages of the present invention will become better understood upon consideration of the following detailed description, drawings and appended claims.

DETAILED DESCRIPTION OF THE INVENTION

Figure 1:
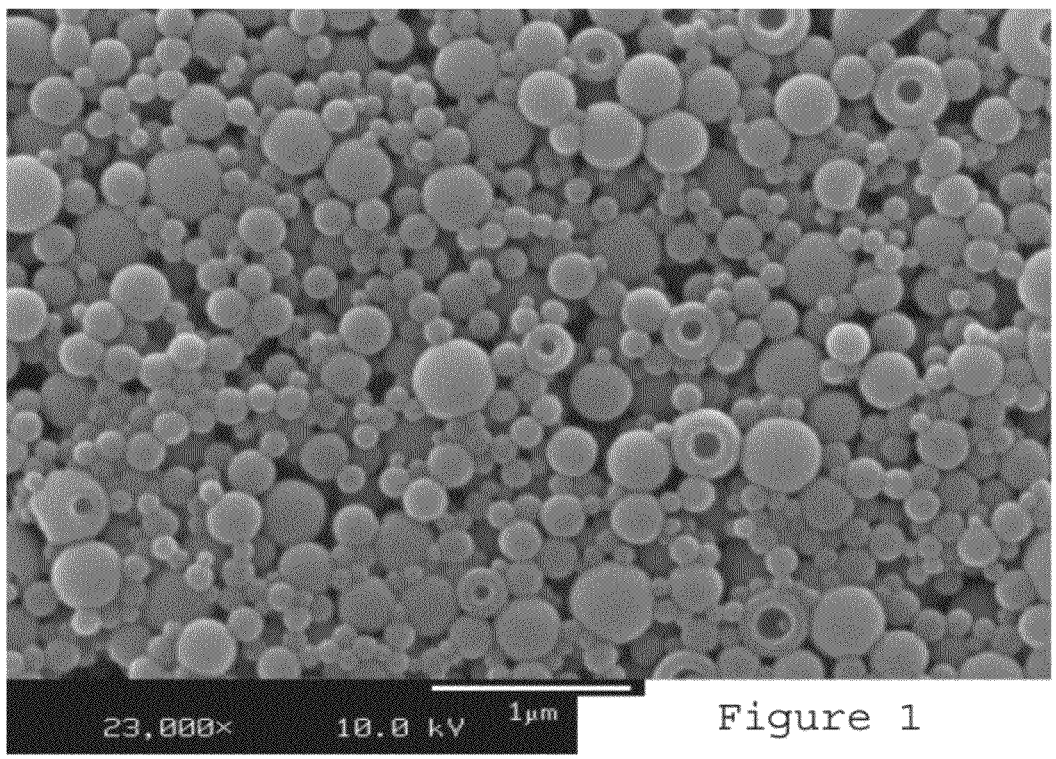
FIG. 1 is a scanning electron microscope (SEM) image of silica-based particles formed using a method of the invention.

The invention provides a method of forming silica-based particles including a polar or non-polar active ingredient. In the method, a polar active ingredient or a non-polar active ingredient, a surfactant, and water are combined and agitated to form an oil-in-water emulsion or a water-in-oil emulsion. One or more silica precursors are added to the oil-in-water emulsion or the water-in-oil emulsion and mixed. At least one of the silica precursors is a functionalized silane. The silica precursors hydrolyze and silica-based particles are formed which encapsulate the polar active ingredient or the non-polar active ingredient.

In one example method according to the invention, an emulsion is prepared wherein the emulsion includes a continuous phase that is polar or non-polar, and a dispersed phase comprising droplets including (i) a polar active ingredient when the continuous phase is non-polar or (ii) a non-polar active ingredient when the continuous phase is polar. A first silica precursor is added to the emulsion such that the silica precursor can be emulsion templated on the droplets to form hollow silica-based particles. The silica precursor has the general formula (I):

$$R^1_x\!\!-\!\!Si\!\!-\!\!(OR^2)_y \qquad (I)$$

wherein $R^1$ is selected from substituted and unsubstituted alkyl, substituted and unsubstituted aryl, alcohols, amines, amides, aldehydes, acids, esters, and functional groups having an unsaturated carbon-carbon bond, $R^2$ is an alkyl group, $x+y=4$, and $y=1$, 2 or 3. $R^1$ and/or $R^2$ can be substituted or unsubstituted, branched or unbranched, $C_1$ to $C_{1000}$ alkyl, or $C_1$ to $C_{100}$ alkyl, or $C_1$ to $C_{50}$ alkyl, or $C_1$ to $C_{25}$ alkyl, or $C_1$ to $C_{10}$ alkyl, or $C_1$ to $C_5$ alkyl.

The $R^1$ group is capable of preventing or limiting aggregation of the particles. The $R^1$ group can include a functional group that allows for attachment of a polymer or other molecular complex to a surface of the particles by covalent linking. The $R^1$ group can have a net charge to attract towards an opposite charge of the surfactant at interfaces between the droplets and the continuous phase. The $R^1$ group can have a charge ratio to limit polar and non-polar penetrations through interfaces between the droplets and the continuous phase to allow better stabilization of the emulsion as well as assist in reactions. At least two of the $R^1$ groups can be selected from functional groups that allow for attachment of a polymer or other molecular complex to a surface of the particles by covalent linking, functional groups having a net charge to attract towards an opposite charge of a surfactant at interfaces between the droplets and the continuous phase, and functional groups having a charge ratio to limit polar and non-polar penetrations through interfaces between the droplets and the continuous phase to allow better stabilization of the emulsion as well as assist in reactions.

The continuous phase can include a compound to control viscosity. The compound for the continuous phase can be selected from water soluble polymers, salts, alcohols, glycols, alkylene ethoxylates, and mixtures thereof. The dispersed phase can include a compound to control viscosity. The compound for the dispersed phase can be selected from oil soluble polymers, waxes, fatty alcohols, triglycerides, fatty acids, fatty amines, esters, hydrocarbons, and mixtures thereof.

A charged polymer can be added to the emulsion. Preferably, the charged polymer is cationic. A ratio of the active ingredient to the charged polymer can be 1:1 to 30:1, 1:1 to 20:1, or 1:1 to 10:1, or 1:1 to 5:1. The charged polymer can be in the continuous phase or the dispersed phase comprising the droplets. When the charged polymer is in the continuous phase, it can provide a coating on the outside surface of the formed silica-based particles. When the charged polymer is in the droplets, it can provide a coating on the inside surface of the formed silica-based particles. The charged polymer can have 2 to 1000, or 5 to 500, or 10 to 100, or 25 to 50 repeat units. The charged polymer can have up to 1,000,000 repeat units. The charged polymer can alkoxylated, preferably ethoxylated, with 1-100 moles of alkoxy groups. A non-limiting example charged polymer is MERQUAT 550 (an aqueous solution of a highly charged cationic copolymer of 30 mole % diallyl dimethyl ammonium chloride and 70 mole % acrylamide).

Optionally, a second silica precursor can be added to the emulsion such that the second silica precursor can be emulsion templated on the droplets or deposited on the hollow silica-based particles to form hollow silica-based particles. The second silica precursor has the general formula (II):

$$R^3{}_m\text{—Si—}(OR^4)_n \quad (II)$$

wherein $R^3$ is selected from substituted and unsubstituted alkyl, substituted and unsubstituted aryl, alcohols, amines, amides, aldehydes, acids, esters, and functional groups having an unsaturated carbon-carbon bond, $R^4$ is an alkyl group, m+n=4, and m=0, 1, 2 or 3. The first silica precursor and the second silica precursor can be added in a ratio from 1:99 to 99:1, or 1:50 to 50:1, or 1:25 to 25:1, or 1:10 to 10:1, or 1:5 to 5:1, or 1:2 to 2:1. $R^3$ and/or $R^4$ can be substituted or unsubstituted, branched or unbranched, $C_1$ to $C_{1000}$ alkyl, or $C_1$ to $C_{100}$ alkyl, or $C_1$ to $C_{50}$ alkyl, or $C_1$ to $C_{25}$ alkyl, or $C_1$ to $C_{10}$ alkyl, or $C_1$ to $C_5$ alkyl.

Optionally, a third silica precursor can be added to the emulsion such that the third silica precursor can be emulsion templated on the droplets or deposited on the hollow silica-based particles to form hollow silica-based particles. The third silica precursor has the general formula (III):

$$R^5{}_a\text{—Si—}(OR^6)_b \quad (III)$$

wherein $R^5$ is selected from substituted and unsubstituted alkyl, substituted and unsubstituted aryl, functional groups having an unsaturated carbon-carbon bond, functional groups having a carboxylic acid group, polymers of alkylene oxide, and aminofunctional groups, $R^6$ is an alkyl group, a+b=4, and a=0, 1, 2 or 3. $R^5$ and/or $R^6$ can be substituted or unsubstituted, branched or unbranched, $C_1$ to $C_{1000}$ alkyl, or $C_1$ to $C_{100}$ alkyl, or $C_1$ to $C_{50}$ alkyl, or $C_1$ to $C_{25}$ alkyl, or $C_1$ to $C_{10}$ alkyl, or $C_1$ to $C_5$ alkyl. The first silica precursor and the third silica precursor can be added in a ratio from 1:99 to 99:1, or 1:50 to 50:1, or 1:25 to 25:1, or 1:10 to 10:1, or 1:5 to 5:1, or 1:2 to 2:1. The second silica precursor and the third silica precursor can be added in a ratio from 1:99 to 99:1, or 1:50 to 50:1, or 1:25 to 25:1, or 1:10 to 10:1, or 1:5 to 5:1, or 1:2 to 2:1.

In certain versions of the above methods of the invention, $R^1$ and/or $R^3$ and/or $R^5$ can be phenyl; $R^1$ and/or $R^3$ and/or $R^5$ and/or be $C_{12}$-$C_{24}$ alkyl; $R^1$ and/or $R^3$ and/or $R^5$ can be substituted or unsubstituted acrylic acid; $R^1$ and/or $R^3$ and/or $R^5$ can be polyethylene glycol; $R^1$ and/or $R^3$ and/or $R^5$ can be alkylamine; $R^1$ and/or $R^3$ and/or $R^5$ can be alkyl carboxylate; or $R^1$ and/or $R^3$ and/or $R^5$ can be alkyl quaternary amine.

The second silica precursor can be added to the emulsion with the first silica precursor, or at a time after the first silica precursor is added, and the first silica precursor and the second silica precursor can be the same or different. The droplets initiate reaction of the first silica precursor and the second silica precursor at interfaces between the droplets and the continuous phase.

A first surfactant can be added to form the emulsion including the continuous phase and the dispersed phase comprising droplets. The surfactant can be selected from cationic, anionic, nonionic and amphoteric surfactants and can be added to a first material comprising the continuous phase and a second material comprising the dispersed phase to form the emulsion. In one version of the method, the surfactant is introduced to the emulsion below a critical micelle concentration of the surfactant for precursor interface interaction. In another version of the method, the surfactant is introduced to the emulsion above a critical micelle concentration of the surfactant. Preferably, the surfactant is cationic.

A second surfactant can be added to form the emulsion including the continuous phase and the dispersed phase comprising droplets. The second surfactant can be added below a critical micelle concentration of the second surfactant for precursor interface interaction, and the second surfactant can be selected from cationic, anionic, nonionic and amphoteric surfactants. The second surfactant can be added above a critical micelle concentration of the second surfactant for precursor interface interaction, and the second surfactant can be selected from cationic, anionic, nonionic and amphoteric surfactants. The surfactant can be added above a critical micelle concentration of the surfactant to stabilize the particles and then diluted to reduce the level of surfactant to maintain the level below the critical micelle concentration of the surfactant before the precursor is added for precursor interaction. The emulsion can have a charge associated with the surfactant to help speed up the reaction at interfaces between the droplets and the continuous phase by targeting and directing precursor formation at interfaces between the droplets and the continuous phase in a quicker fashion.

The particles prepared by the method can be spherical, and/or monopore. The emulsion can include two or more oils which remain as a core of a silica particle shell after drying. At least one oil remains in a silica particle shell after being washed. In one method, the particle shell formation occurs for 10 minutes to 48 hours, and the particles are precipitated out. After precipitation, the particles can be washed with a 0.1% to 10% solution of a monovalent salt, such as NaCl or KCl. This shrinks the pore size and maintains shape of the oil. The silica particles can be modified from a continuously formed shell to a partially formed hollow shell by adjusting a ratio of the first silica precursor and the second silica precursor in the emulsion. The silica particle can lose its internal core due to partial formation from a limited molar ratio of the first silica precursor and the second silica precursor. The silica particle can include a partially formed shell from aid of precursor hindrance from the $R^1$ group. The silica particle can allow for one or more particles of smaller size either with a pore or continuous shell to be present in the partially formed shell.

In one version of the method, the $R^1$ groups are capable of attaching a coating by covalent bonding, non-covalent bonding, ionic bonding, electrostatic attraction, or any other attachment mechanism which allows for coating proximity within sub-nanometer ranges to 500 microns. The coating can comprise a polymeric material.

In another version of the method, the particles have multiple layering effects while trapping an active material inside these layers. The particle can have 1 to 100 layers of silica deposited when the first silica precursor and the second silica precursor are templated on a droplet. The particle can burst upon friction and release a payload contained within the particle. The particle can remain intact within environments of pH ranges from 0.01-14. The particle can be chemically altered and open for diffusion of a payload contained within the particle.

In one version of the method, the first silica precursor leaves a first shell thickness of 1 nanometer to 500 nanometers for the particle when the first silica precursor and the second silica precursor are templated on a droplet. The second silica precursor can bond to the first shell to create an outer layer such that the first shell and the outer layer together have a thickness in the range of 1 nanometer to 1 micron. The particle can form making a shell with a thickness of 1 nanometer to 5 microns. The particle can have an overall size of 10 nanometers to 250 microns. The particle can include an oil droplet having a size of 1 nanometer to 200 microns. The particle can maintain a template volume of greater than 0.01%. The particle can maintain a template volume up to 100% loading. The particle can maintain greater than 0.01% of a loaded material if the loaded material dissipates or leaches from the particle. The particle can allow for complete release of a payload material from the particle when the particle is intact or ruptured. The particle can release one layer of a loaded material at a time. The particle can release multiple layers of a loaded material at a time. The particle can release a loaded material due to coating dissociation.

A templated silica particle formed from the method of the invention can be dispersed in a carrier of polarity opposite to the active ingredient, and the particle can release the active ingredient due to bulk phase evaporation of the carrier. The particle can remain completely or partially intact due to a coating on the particle. The particle can include an oil with a mixture of solids, semi solids, or other liquids or gases. The particle can have water soluble constituents mixed in an oil forming the emulsion for the templating.

In one form, the templated silica particle has a zeta potential ranging from −80 mV to 150 mV. The zeta potential can be measured on a Zetasizer instrument from Malvern Instruments, Malvern, UK, or on a ZetaPlus or ZetaPALS instrument from Brookhaven Instruments, Holtsville, N.Y. In some embodiments, the templated silica particles have a zeta potential of at least about 5, 10, 12, 14, 16, 18, 20, 25, 30, 35, 40, 45, 50, 55, 60, 65, 70, 80, 90 or 100 mV. In some embodiments, the templated silica particles have a zeta potential of no more than about 15, 20, 25, 30, 35, 40, 45, 50, 55, 60, 65, 70, 80, 90, 100, or 150 mV. In some embodiments the zeta potential is between 10 and 70 mV, between 20 and 65 mV, between 25 and 65 mV, between 30 and 60 mV, between 30 and 100 mV, between 40 and 80 mV, between 70 and 100 mV or between 40 and 55 mV.

In a non-limiting example of the invention, an emulsion is formed by homogenizing a mixture of oil (e.g., fragrance as an active ingredient) and a surfactant solution using a Polytron 3100 homogenizer. This process usually runs from 10-60 minutes. Then an oil in water emulsion is formed with the desired oil droplet sizes. A certain volume of this emulsion is transferred to a reaction container for the emulsion templating reaction. Ammonium hydroxide is first added to the emulsion solution as basic catalyst for the sol-gel reaction with stirring. A pH of 8-12 and preferably 9-11 is used. Then a first silica precursor is introduced for the preliminary silica shell formation around the surfactant stabilized oil droplets and the reaction solution is stirred for a time period of anywhere between 2-24 hours. After this step, a second silica precursor is introduced over 30-60 minutes under stirring for the thickening of the shell and then after some time the stirring is stopped and the reaction solution is allow to sit for up to 2 days depending on what shell thickness is desired for the hollow silica-based particles. Alternatively, the time periods for addition of the first silica precursor and the second silica precursor can overlap. Preferably, the first silica precursor and the second silica precursor are different. The silica particles formed can be modified from continuously formed hollow shells to partially formed hollow shells by adjusting a ratio of the two silica precursors in the emulsion. Optionally, three or more silica precursors can be used in the emulsion.

After the reaction is completed, a small volume of the reaction solution is transferred into a vial for washing with water using a centrifuge for about 3 times. At the end of washing, this solution is used to prepare scanning electron microscope samples for investigation of the shell formation and size distribution. A vacuum filter with the appropriate membrane pore size are used to collect the silica-based shells dry for long term storage.

In this example version of the invention, a unique emulsion system is formed in the aqueous phase that stabilizes the emulsion, preventing the coalescence of the oil droplets while the organic silica precursor is reacting.

Active ingredients can be encapsulated within the hollow silica-based particles of the invention. The particles can be viewed as having two parts, the core and the shell. The core contains the active ingredient, while the shell surrounds and protects the core. The core materials used in the invention can be solid or liquid, and if liquid, can be, for example, in the form of a pure compound, solution, dispersion or emulsion. The shell material can be a silica-based shell. The shell can be made permeable, semi-permeable or impermeable. Permeable and semi-permeable shells can be used for release applications. A permeable shell can be a shell including one or more passageways that extend from an inner surface of the shell (which is around the core) and the outer surface of the shell. Semi-permeable shells can be made to be impermeable to the core material but permeable to low molecular-weight liquids and can be used to absorb substances from the environment and to release them again when brought into another medium. The impermeable shell encloses the core material. To release the content of the core material, the shell must be ruptured.

The ceramic shells are prepared by a sol-gel based process in which a silica precursor is used. There are many silica precursors which can used in the present invention. For example, the silica precursor can be a silicon alkoxide (e.g. from silicon methoxide to silicon octadecyloxide), or a functionalized alkoxides (such as ethyltrimethoxysilane, aminopropyltriethoxysilane, vinyltrimethoxysilane, diethyldiethoxysilane, diphenyldiethoxysilane, etc). Further specific examples of silica precursors include tetramethoxysilane (TMOS), tetraethoxysilane (TEOS), tetrabutoxysilane (TBOS), tetrapropoxysilane (TPOS), polydiethoxysilane, methyltrimethoxysilane, methyltriethoxysilane, ethyltriethoxysilane, and phenyltriethoxysilane. The silica precursor may include, for example, from one to four alkoxide groups each having from 1 or more oxygen atoms, and from 1 to 18 carbon atoms, more typically from 1 to 5 carbon atoms. The alkoxide groups may be replaced by one or more suitable functional groups. Examples of functional groups attached to silica precursors include alkyls, aryls, alcohols, amines, amides, aldehydes, acids, esters, and groups including an unsaturated bond. Thus, an organically modified silica precursor can be used. An organically modified silica precursor can be a silica precursor wherein one or two (out of four) of the alkoxysilane groups has been replaced by organic groups like alkyls, aryls, alcohols, amines, amides, aldehydes, acids, esters, and groups including an unsaturated bond. The processing is based on the hydrolysis and condensation of the silica precursors. Water is thus typically used as the condensing agent.

Various surfactants can be used in the method of the invention. In order to form an oil-in-water emulsion of the invention, surfactants with an HLB value above about 8 are generally used. In some cases, multiple surfactants are used as a blend. Where there are multiple surfactants, the combined HLB of the surfactants is generally used. The HLB of the surfactant or surfactants is between, for example, 7 and 13, 8 and 12, 9 and 11, 9.5 and 10.5. In some embodiments, the HLB of the surfactants is 8, 8.5, 9, 9.5, 10, 10.5, 11, 11.5, or 12. Surfactants suitable for forming the oil-in-water emulsion include anionic, non-ionic, cationic, and zwitterionic surfactants. Non-limiting example surfactants include: anionic—sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps; cationic—dimethylammonium and trimethylammonium surfactants of chain length from 8 to 20 and with chloride, bromide or sulfate counterion, myristyl-gammapicolinium chloride and relatives with alkyl chain lengths from 8 to 18, benzalkonium benzoate, double-tailed quaternary ammonium surfactants with chain lengths between 8 and 18 carbons and bromide, chloride or sulfate counterions; nonionic: surfactants of the form $C_n(EO)_m$ where the alkane chain (C) length n is from 6 to 20 carbons and the average number of ethylene oxide (EO) groups m is from 2 to 80, ethoxylated cholesterol; zwitterionics and semipolars—N,N,N-trimethylaminodecanoimide, amine oxide surfactants with alkyl chain length from 8 to 18 carbons, dodecyldimethylammoniopropane-1-sulfate, dodecyldimethylammoniobutyrate, dodecyltrimethylene di(ammonium chloride), decylmethylsulfonediimine, dimethyleicosylammoniohexanoate and relatives of these zwitterionics and semipolars with alkyl chain lengths from 8 to 20.

In order to form the water-in-oil emulsion of the invention, surfactants with an HLB value below about 8 are generally used. In some cases, multiple surfactants are used as a blend. Where there are multiple surfactants, the combined HLB of the surfactants is generally used. The HLB of the surfactant or surfactants is between, for example, 2 and 7, 3 and 6, 4 and 5, or 3.5 and 4.5. In some embodiments, the HLB of the surfactants is 2, 2.5, 3, 3.5, 4, 4.5, 5, 5.5 or 6. Surfactants suitable for forming the water-in-oil emulsion include anionic, non-ionic, cationic, and zwitterionic surfactants. Non-limiting example surfactants include: anionic—sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps; cationic—dimethylammonium and trimethylammonium surfactants of chain length from 8 to 20 and with chloride, bromide or sulfate counterion, myristyl-gammapicolinium chloride and relatives with alkyl chain lengths from 8 to 18, benzalkonium benzoate, double-tailed quaternary ammonium surfactants with chain lengths between 8 and 18 carbons and bromide, chloride or sulfate counterions; nonionic: surfactants of the form $C_n(EO)_m$ where the alkane chain (C) length n is from 6 to 20 carbons and the average number of ethylene oxide (EO) groups m is from 2 to 80, ethoxylated cholesterol; zwitterionics and semipolars—N,N,N-trimethylaminodecanoimide, amine oxide surfactants with alkyl chain length from 8 to 18 carbons, dodecyldimethylammoniopropane-1-sulfate, dodecyldimethylammoniobutyrate, dodecyltrimethylene di(ammonium chloride), decylmethylsulfonediimine, dimethyleicosylammoniohexanoate and relatives of these zwitterionics and semipolars with alkyl chain lengths from 8 to 20. Isocetyl alcohol is also a suitable emulsifier.

Cationic surfactants may be especially beneficial when used in the method of the invention. The condensation reaction occurs at basic pH and therefore, any hydrolyzed silica precursor is deprotonated and therefore negative at basic pH. When a cationic surfactant is present at the dispersed phase-continuous phase interface, this drives the deprotonated hydrolyzed silica precursor to the interface thereby speeding up the reaction time. In addition, any positive charges on functional groups of the hydrolyzed silica precursor can drive further deprotonated hydrolyzed silica precursor to the interface thereby speeding up the reaction time.

Various polar or non-polar active ingredients can be used in the invention depending on the final use for the silica-based particles. Non-limiting examples for the active ingredient include sunscreens, steroidal anti-inflammatory actives, analgesic actives, antifungals, antibacterials, antiparasitics, antivirals, anti-allergenics, anti-cellulite additives, medicinal actives, skin rash, skin disease and dermatitis medications, insect repellant actives, antioxidants, hair growth promoter, hair growth inhibitor, hair bleaching agents, deodorant compounds, sunless tanning actives, skin lightening actives, anti-acne actives, anti-skin wrinkling actives, anti-skin aging actives, vitamins, nonsteroidal anti-inflammatory actives, anesthetic actives, anti-pruritic actives, anti-microbial actives, dental care agents, personal care agents, nutraceuticals, pharmaceuticals, fragrances, antifouling agents, pesticides, lubricants, etchants, and mixtures and combinations thereof. In one example embodiment, the non-polar active ingredient is a fragrance. In another example embodiment, the non-polar active ingredient is a sunscreen.

The size of the silica-based particles formed is determined, at least in part, by the conditions of the reaction including the size of the original emulsion, and the conditions used for formation of the silica-based particles. A distribution of particle sizes can be obtained, or particles of a uniform size can be formed. The silica-based particles can also be fractionated into a desired size range after formation. Fractionation can be carried out by methods known in the art such as selective precipitation, or by using filters or sieves in order to pass a selected size range and retain the rest. The size of the silica-based particles can be modified in order to suit a particular application.

In some embodiments, the mean size of the hollow silica-based particles is between 10 nanometers and 1 millimeter, between 10 nanometers and 1 μm, between 1 μm and 100 μm, between 10 μm and 50 μm, between 50 μm and 200 μm, or between 200 μm and 500 μm. In some embodiments, the mean size of the silica-based particles is between 1 nanometer and 10 nanometers, between 10 nanometers and 100 nanometers, between 100 nanometers and 1 μm, between 150 nanometers and 800 nanometers, between 1 μm and 5 μm, between 1 μm and 10 μm, between 5 μm and 10 μm, between 1 μm and 20 μm, between 10 μm and 20 μm, between 10 μm and 100 μm, between 100 μm and 1 millimeter, between 1 millimeter to 10 millimeters, or larger. In some embodiments, the mean size of the silica-based particles is within plus or minus 10% of 1 nanometer, 10 nanometers, 25 nanometers, 50 nanometers, 75 nanometers, 90 nanometers, 100 nanometers, 250 nanometers, 500 nanometers, 750 nanometers, 900 nanometers, 1 μm, 5 μm, 10 μm, 25 μm, 50 μm, 75 μm, 90 μm, 100 μm, 250 μm, 500 μm, 750 μm, 900 μm, 1 millimeter, or larger. In some embodiments, the mean size of the silica-based particles is within plus or minus 50% of 1 nanometer, 10 nanometers, 25 nanometers, 50 nanometers, 75 nanometers, 90 nanometers, 100 nanometers, 250 nanometers, 500 nanometers, 750 nanometers, 900 nanometers, 1 μm, 5 μm, 10 μm, 25 μm, 50 μm, 75 μm, 90 μm, 100 μm, 250 μm, 500 μm, 750 μm, 900 μm, 1 millimeter, or larger. In some embodiments, the silica-based particles are monodisperse.

The ratio of silica precursor(s) to that of the active ingredient may vary from 0.1:1 to 100:1, preferably from 0.5:1 to 50:1, more preferably from 1:1 to 20:1, and most preferably from 1:1 to 10:1. The silica precursor and the second silica precursor can be added in a ratio from 1:99 to 99:1, or 1:50 to 50:1, or 1:25 to 25:1, or 1:5 to 15:1, or 1:1 to 10:1. The second silica precursor and the third silica precursor can be added in a ratio from 1:99 to 99:1, or 1:50 to 50:1, or 1:25 to 25:1, or 1:5 to 15:1, or 1:1 to 10:1.

The invention is further illustrated in the following Examples which are presented for purposes of illustration and not of limitation.

EXAMPLES

Example 1

An emulsion was formed by homogenizing a mixture of 5% of oil fragrance and 0.2% of a surfactant solution of Triton™ X-100 non-ionic surfactant (Octylphenol Ethoxylate, R—$C_6H_4$—O—$(CH_2CH_2O)_x$—H where R=octyl (C8) and x=9.5 avg.) using a Polytron 3100 homogenizer. This process ran for 30 minutes. An oil in water emulsion was formed with the desired oil droplet sizes. A volume of 25 milliliters of this emulsion was transferred to a reaction container for an emulsion templating reaction. Ammonium hydroxide was first added at 2% to the emulsion solution as catalyst for the sol-gel reaction with stirring, then 1 milliliter of a first silica precursor, phenyltriethoxysilane, was introduced for the preliminary silica shell formation around the surfactant stabilized oil droplets and the reaction solution was stirred for a time period of 2 hours. After this step, 0.125 milliliters of a second silica precursor, tetramethoxysilane (TMOS), was introduced over 30 minutes under stirring for the thickening of the shell and then after some time the stirring was stopped and the reaction solution was allowed to sit for 1-2 days for the hollow silica-based particles. After the reaction was complete, a small volume of the reaction solution was transferred into a vial for washing with water using a centrifuge for three times. At the end of washing, this solution was used to prepare scanning electron microscope samples for investigation of the shell formation and size distribution.

FIG. 1 shows a first SEM image of silica-based particles formed using the emulsion templating reaction of the invention. Note in FIG. 1 how the dual precursor, oil in water emulsion of the invention produced silica-based particles in the range of 150-800 or 700-900 nanometers. In the SEM image of FIG. 1, the presence of hollow particles having a continuously formed shell and hollow particles having a partially formed hollow shell can be seen. The formation of continuously formed shells or partially formed hollow shell can be adjusted by the ratio of the two silica precursors in the emulsion. Limited moles of silica precursor can provide monopore shells as shown in FIG. 1. Furthermore, in the SEM image of FIG. 1, the presence of a particle of smaller size within a pore of a larger shell can be seen.

Figure 2:
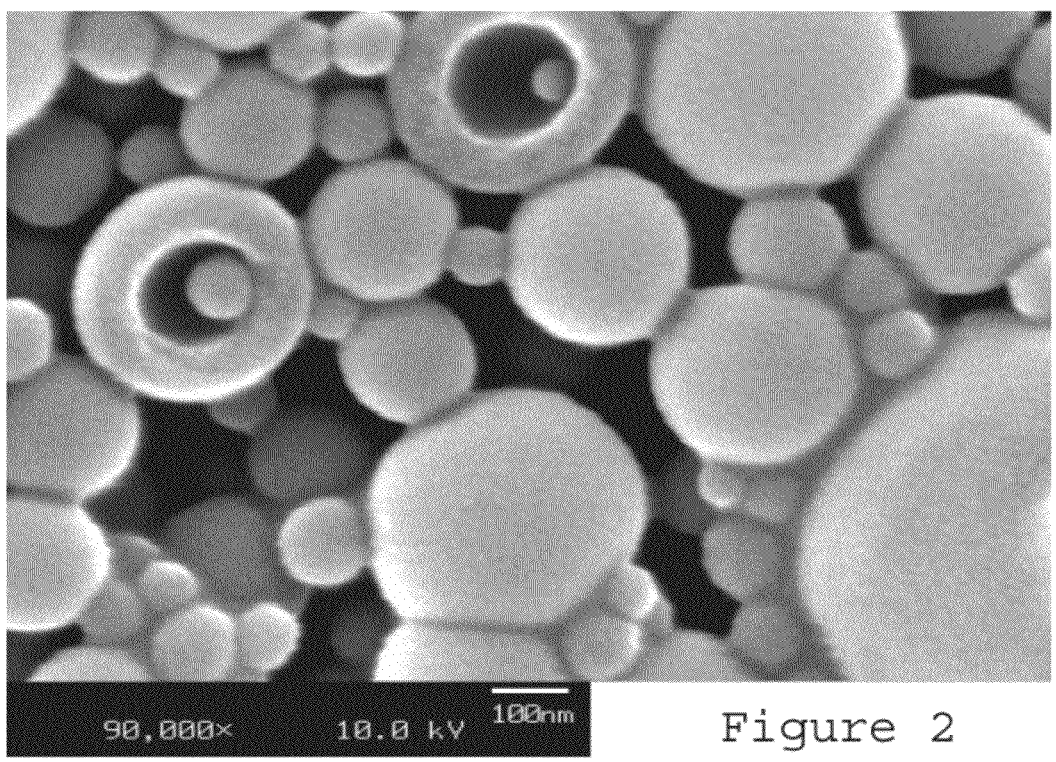
FIG. 2 is another SEM image of silica-based particles formed using a method of the invention.

FIG. 2 shows a second SEM image of silica-based particles formed using this method of the invention. In the SEM image of FIG. 2, the presence of a particle of smaller size within a pore of a larger shell can be seen. Without intending to be bound by theory, it is believed that the hydrophobic interior of the larger shell particle pulls the smaller particle into the pore of the larger particle. Alternatively, particles formed by the second silica precursor may form in the pore of the larger particle.

Figure 3:
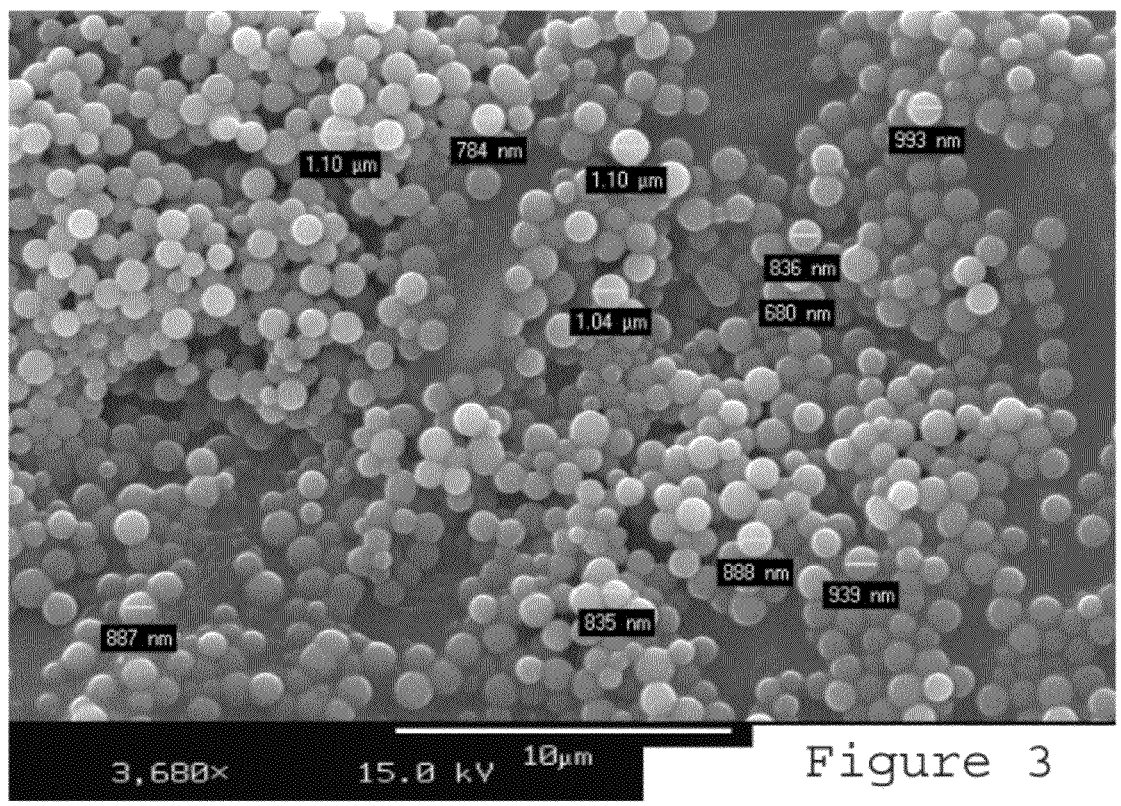
FIG. 3 is yet another SEM image of silica-based particles formed using a method of the invention.

FIG. 3 shows a third SEM image of silica-based particles formed using this method of the invention. In the SEM image of FIG. 3, the presence of particles of uniform size can be seen. Uniform particles having a size above 1 micron are present.

Figure 4:
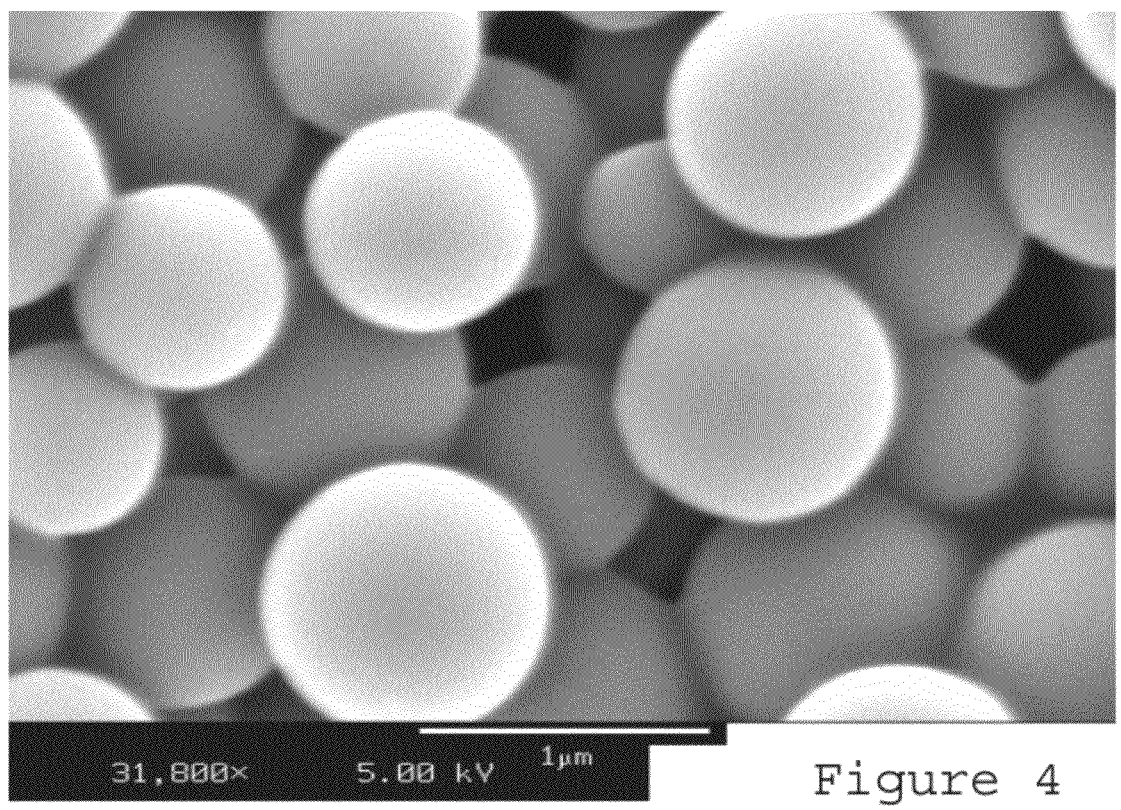
FIG. 4 is still another SEM image of silica-based particles formed using a method of the invention.

FIG. 4 shows a fourth SEM image of silica-based particles formed using this method of the invention. In the SEM image of FIG. 4, the particles are generally smooth. However, the small fuzziness on the particle surfaces is believed to be an indicator of the functional groups of the modified silica precursor on the surface. Also, certain particles in FIG. 4 show binding at contact areas which is an indication of covalent linking.

Figure 5:
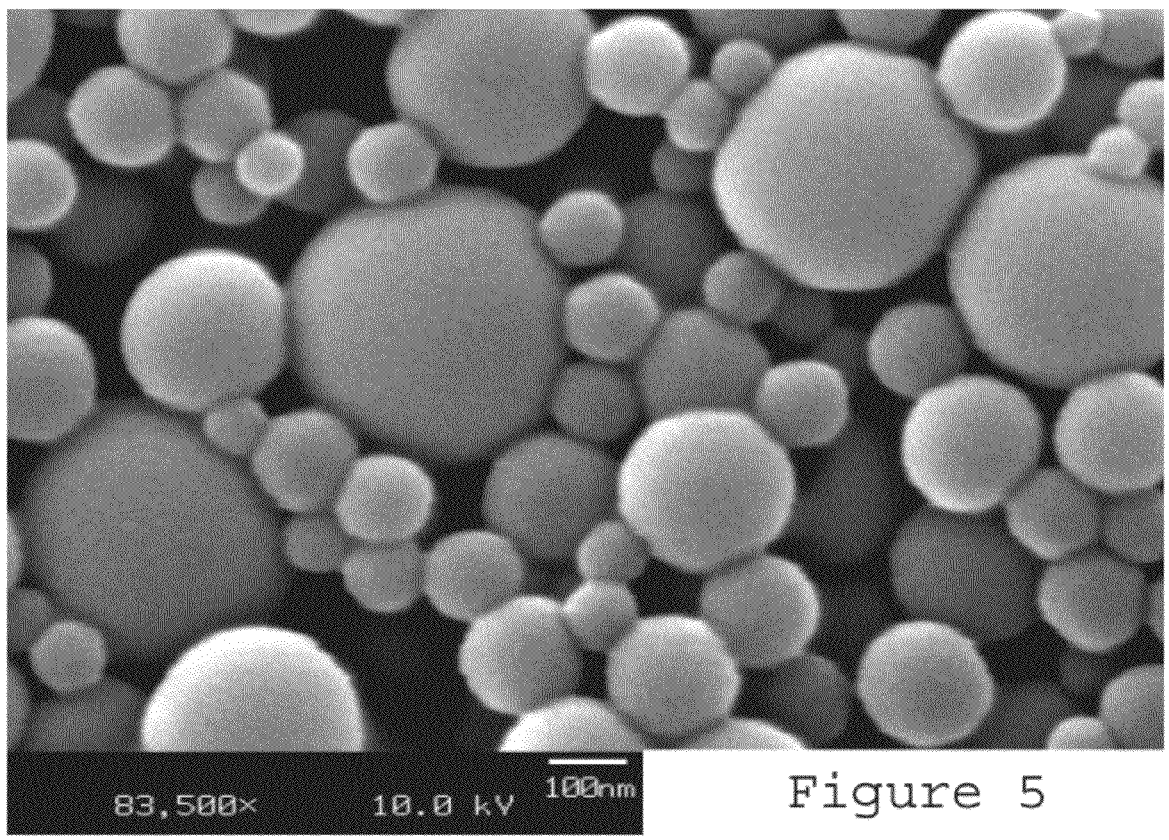
FIG. 5 is yet another SEM image of silica-based particles formed using a method of the invention.

FIG. 5 shows a fifth SEM image of silica-based particles formed using the method of the invention. In the SEM image of FIG. 5, the presence of spherical particles of a size below 100 nanometers can be seen. Also, a shell having a pore (i.e., a partially formed hollow shell) can be seen.

Figure 6:
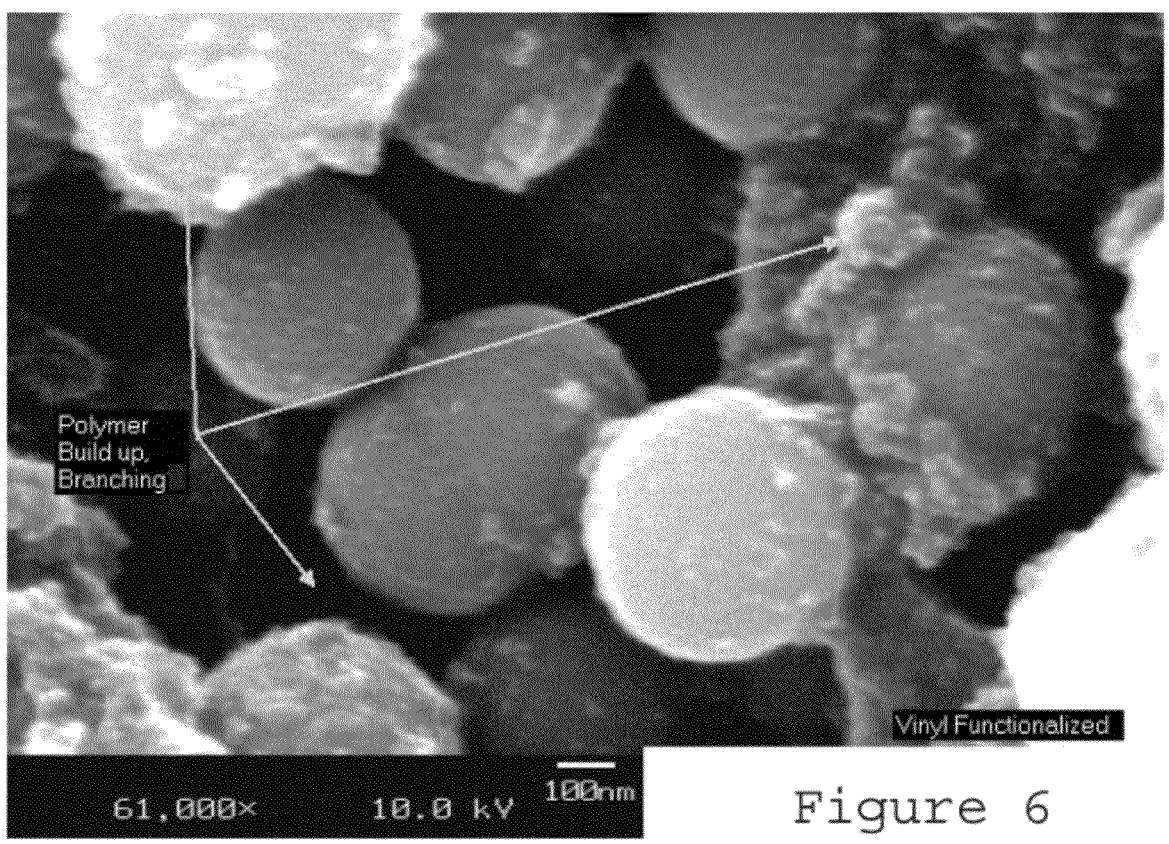
FIG. 6 is still another SEM image of silica-based particles formed using a method of the invention.

FIG. 6 shows a sixth SEM image of silica-based particles formed using this method of the invention wherein the aqueous phase included a water soluble polymer (e.g., polymethylmethacrylate). The roughened surface shown in FIG. 6 indicates polymer build up and branching between the vinyl functionalized surface of the shell of the particles. Thus, these particles have functional groups capable of attaching a coating by covalent bonding, non-covalent bonding, ionic bonding, electrostatic attraction, or any other attachment mechanism.

Example 2

An emulsion was formed by homogenizing a mixture of 0.75 grams of oil fragrance and 23.85 milliliters of water and 0.04 grams of a surfactant solution of Triton™ X-100 non-ionic surfactant (Octylphenol Ethoxylate, R—$C_6H_4$—O—$(CH_2CH_2O)_x$—H where R=octyl (C8) and x=9.5 avg.) using a Polytron 3100 homogenizer. This process ran for 30 minutes. An oil in water emulsion was formed with the desired oil droplet sizes. Ammonium hydroxide was added at 1.25 milliliters to the emulsion solution as catalyst for the sol-gel reaction with stirring, then 1.5 milliliters of a first silica precursor, phenyltriethoxysilane, was introduced for the preliminary silica shell formation around the surfactant stabilized oil droplets and the reaction solution was stirred for a time period of 2 hours. After this step, 0.125 milliliters of a second silica precursor, aminopropyltriethoxysilane, was introduced over 30 minutes under stirring for the thickening of the shell and then after some time the stirring was stopped and the reaction solution was allowed to sit for 1-2 days for the hollow silica-based particles. After the reaction was complete, a small volume of the reaction solution was transferred into a vial for washing with water using a centrifuge for three times. At the end of washing, this solution was used to prepare scanning electron microscope samples for investigation of the shell formation and size distribution. Very nice micron shells with minimal small ones were identified.

Example 3

An emulsion was formed by homogenizing a mixture of 0.5 grams of oil fragrance, 47.6 milliliters of water, 0.5 grams of a 10% solution of MERQUAT 550 (an aqueous solution of a highly charged cationic copolymer of 30 mole % diallyl dimethyl ammonium chloride and 70 mole % acrylamide), and 0.4 grams of a 10% surfactant solution of Triton™ X-100 non-ionic surfactant (Octylphenol Ethoxylate, R—$C_6H_4$—O—$(CH_2CH_2O)_x$—H where R=octyl (C8) and x=9.5 avg.) using a Polytron 3100 homogenizer. This process ran for 30 minutes. An oil in water emulsion was formed with the desired oil droplet sizes. Ammonium hydroxide was added at 2.5 milliliters to the emulsion solution as catalyst for the sol-gel reaction with stirring, then 2.5 milliliters of phenyltriethoxysilane was introduced for the silica shell formation around the surfactant stabilized oil droplets and the reaction solution was stirred for a time period of 2 hours. The stirring was stopped and the reaction solution was allowed to sit for 1-2 days for the hollow silica-based particles. After the reaction was complete, a small volume of the reaction solution was transferred into a vial for washing with water using a centrifuge for three times. At the end of washing, this solution was used to prepare scanning electron microscope samples for investigation of the shell formation and size distribution. Complete shells were identified.

Thus, the invention provides a method for forming hollow silica-based particles suitable for containing one or more active ingredients or for containing other smaller particles which may include one or more active ingredients.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for forming silica-based particles, the method comprising:
   (a) preparing an emulsion including a cationic polymer and having a continuous phase that is polar or nonpolar, and a dispersed phase comprising droplets including (i) one or more polar active ingredients when the continuous phase is non-polar or (ii) one or more non-polar active ingredients when the continuous phase is polar;
   (b) adding a first silica precursor to the emulsion such that the silica precursor is emulsion templated at a basic pH of between 8-12 onto the surface of the droplets to form a silica-based first shell layer around the droplets, wherein the first silica precursor has the general formula (I):

$$R^1_x\text{—Si—}(OR^2)_y \quad (I)$$

wherein $R^1$ is a substituted or unsubstituted $C_{12}$-$C_{24}$ alkyl or a substituted or carboxylate or an alkyl quaternary amine, and $R^2$ is an alkyl group, x+y=4, and y=1, 2 or 3; and
   (c) adding a second silica precursor to the emulsion such that the second silica precursor can be emulsion templated onto the surface of the droplets or deposited on the silica-based first shell layer, wherein the second silica precursor has the general formula (II):

$$R^3_m\text{—Si—}(OR^4)_n \quad (II)$$

wherein $R^2$ is selected from substituted and unsubstituted alkyl, substituted and unsubstituted aryl, alcohols, amines, amides, aldehydes, acids, esters, and functional groups having an unsaturated carbon-carbon bond, $R^4$ is an alkyl group, m+n=4, and m=0, 1, 2 or 3,
   wherein the method produces silica-based particles having a silica-based shell surrounding a liquid core comprising the one or more polar active ingredients or the one or more non-polar active ingredients, wherein the silica-based particles have an overall size of 10 nanometer to 250 microns.

2. The method of claim 1 further comprising;
   (d) adding a third silica precursor to the emulsion such that the third silica precursor can be emulsion templated onto the surface of the droplets or droplets or deposited on the silica-based first and/or second shell layers, wherein the third silica precursor has the general formula (III):

$$R^5_a\text{—Si—}(OR^6)_b \quad (III)$$

wherein $R^5$ is selected from substituted and unsubstituted alkyl, substituted and unsubstituted aryl, alcohols, amines, amides, aldehydes, acids, esters, and functional groups having an unsaturated carbon-carbon bond, $R^6$ is an alkyl group, a+b=4, and a=0, 1, 2 or 3.

3. The method of claim 1 wherein the first silica-based shell layer is a continuously formed shell or a partially formed shell.

4. The method of claim 1 wherein the first shell layer has a first shell layer thickness of from sub-nanometer ranges to 500 nanometers when the first silica precursor and the second silica precursor are templated onto the surface of the droplets, and wherein the first shell layer and the second shell layer together have a thickness in the range of 1 nanometer to 1 micron when the second silica precursor bonds to the first shell layer.

5. The method of claim 1 wherein the $R^1$ groups are capable of attaching a coating by covalent bonding, noncovalent bonding, ionic bonding, electrostatic attraction, or any other attachment mechanism which allows for coating proximity within sub-nanometer ranges to 500 microns.

6. The method of claim 5 wherein the coating comprises a polymeric material.

7. The method of claim 1 wherein step (a) comprises adding a surfactant selected from cationic, anionic, nonionic and amphoteric surfactants to a first material comprising the continuous phase and a second material comprising the dispersed phase to form the emulsion.

8. The method of claim 7 wherein the surfactant is cationic.

9. The method of claim 7 wherein step (a) comprises adding a second surfactant.

10. The method of claim 7 wherein the $R^1$ group has a net charge to attract towards an opposite charge of the surfactant at interfaces between the droplets and the continuous phase.

11. The method of claim 1, wherein the cationic polymer is located in the continuous phase.

12. The method of claim 1, wherein the cationic polymer is located in the dispersed phase.

13. The method of claim 1, wherein the basic pH is between 9-11.

14. The method of claim 1, wherein the first and second silica precursors form templated silica particles has a Zeta potential ranging from −80 mV to 150 mV.

15. The method of claim 1, wherein the silica-based particles include an oil droplet having a size of 1 nanometer to 200 microns.

16. The method of claim 1, wherein the ratio of the one or more polar active ingredients or the one or more non-polar active ingredients to the cationic polymer is from 1:1 to 30:1, 1:1 to 20:1, 1:1 to 10:1, or 1:1 to 5:1.

17. The method of claim 1, wherein the ratio of the first silica precursor to the second silica precursor is from 1:99 to 99:1, 1.50 to 50:1, 1:25 to 25:1, 1:10 to 10:1, 1:5 to 5:1, or 1.2 to 2:1.

18. The method of claim 1, wherein the ratio of the first silica precursor to the third silica precursor is from 1:99 to 99:1, 1:50 to 50:1, 1:25 to 25:1, 1:10 to 10:1, 1:5 to 5:1, or 1:2 to 2:1.

19. The method of claim 1, wherein the one or more polar active ingredients or the one or more non-polar active ingredients is a cosmetic product, a detergent product, or oral hygiene product.

20. The method of claim 19, wherein the cosmetic product is a skin cream or a sunscreen formulation.

21. The method of claim 19, wherein the detergent product is a laundry wash product, a household cleaner, a shampoo, a hair conditioner or a bleach.

22. The method of claim 19, wherein the oral hygiene products toothpaste.

23. The method of claim 1, wherein the one or more polar active ingredients or the one or more non-polar active ingredients is a pharmaceutical or a nutraceutical, or mixtures and combinations thereof.

24. The method of claim 1, wherein the one or more polar active ingredients or the one or more non-polar active ingredients is a pharmaceutical or a nutraceutical.

25. The method of claim 1, wherein the one or more polar active ingredients or the one or more non-polar active ingredients is a sunscreen, a steroidal anti-inflammatory active, an analgesic active, an antifungal, an antibacterial, an antiparasitic, an anti-viral, an anti-allergenic, an anti-cellulite additive, a medicinal active, a skin rash medication, a skin disease medication, a dermatitis medication, an insect repellant active, an antioxidant, a hair growth promoter, a hair growth inhibitor, a hair bleaching agent, a deodorant compound, a sunless tanning active, a skin lightening active, an anti-acne active, an anti-skin wrinkling active, an anti-skin aging active, a vitamin, a nonsteroidal anti-inflammatory active, an anesthetic active, an anti-pruritic active, an anti-microbial active, a dental care agent, a personal care agent, a fragrance, an antifouling agent, a pesticide, a lubricant, an etchant, or mixtures and combinations thereof.

* * * * *